United States Patent
Schwarz et al.

(10) Patent No.: US 9,364,605 B2
(45) Date of Patent: Jun. 14, 2016

(54) HAND PIECE ASSEMBLY FOR A DISPOSABLE FLUSHING NOZZLE UNIT FOR CLEANSING AND/OR IRRIGATING SURGICAL WOUNDS

(75) Inventors: Volker A. Schwarz, Steinach (DE); Andreas Gunzl, Thyrnau (DE)

(73) Assignee: Volker A. Schwarz (DE)

( * ) Notice: Subject to any disclaimer, the term of this patent is extended or adjusted under 35 U.S.C. 154(b) by 1207 days.

(21) Appl. No.: 13/195,448

(22) Filed: Aug. 1, 2011

(65) Prior Publication Data
US 2012/0035545 A1  Feb. 9, 2012

(30) Foreign Application Priority Data
Aug. 3, 2010 (DE) .......................... 10 2010 033 240

(51) Int. Cl.
*A61M 3/00* (2006.01)
*A61M 3/02* (2006.01)
*A61M 1/00* (2006.01)

(52) U.S. Cl.
CPC ........... *A61M 3/0258* (2013.01); *A61M 1/0064* (2013.01)

(58) Field of Classification Search
CPC  A61M 3/0258; A61M 1/0039; A61M 1/0064
See application file for complete search history.

(56) References Cited

U.S. PATENT DOCUMENTS

| | | | |
|---|---|---|---|
| 5,470,305 A | 11/1995 | Arnett et al. | |
| 2003/0036723 A1 | 2/2003 | Henniges et al. | |
| 2008/0033348 A1* | 2/2008 | Bidoia | 604/35 |
| 2008/0319379 A1 | 12/2008 | Bidoia | |
| 2009/0281454 A1 | 11/2009 | Baker et al. | |
| 2011/0224600 A1 | 9/2011 | Orlandi | |

FOREIGN PATENT DOCUMENTS

| | | |
|---|---|---|
| EP | 1256322 B1 | 12/2005 |
| WO | WO 2006040273 A1 | 4/2006 |
| WO | WO 2010016089 A2 | 2/2010 |

OTHER PUBLICATIONS

Search Report from the European Patent Office in European Patent Application No. EP 11005501.

* cited by examiner

*Primary Examiner* — Aarti B Berdichevsky
(74) *Attorney, Agent, or Firm* — Erickson Kernell Derusseau & Kleypas, LLC

(57) ABSTRACT

The invention relates to a hand piece for a disposable flushing nozzle unit for cleansing and/or irrigating surgical wounds, comprising a housing with one first connecting unit for holding the disposable flushing nozzle unit, a drive mechanism and an electric motor interacting with said drive mechanism. In an especially advantageous embodiment the hand piece comprises a second connecting unit for connecting an external electric power supply.

9 Claims, 4 Drawing Sheets

HAND PIECE ASSEMBLY FOR A DISPOSABLE FLUSHING NOZZLE UNIT FOR CLEANSING AND/OR IRRIGATING SURGICAL WOUNDS

CROSS-REFERENCE TO RELATED APPLICATIONS

This application claims priority from German Application No. DE 10 2010 033 240.2 filed Aug. 3, 2010, the contents of which are incorporated herein by this reference.

BACKGROUND OF THE INVENTION

The invention relates to a hand piece assembly for a disposable flushing nozzle unit for cleansing and/or irrigating surgical wounds.

Cleansing assemblies for cleansing and/or irrigating surgical wounds are well known in the prior art. Such cleansing assemblies are also referred to in the prior art as "pulse lavage" systems, which in addition to cleansing contaminated wounds are also used for effective intra-operative irrigation of wounds, for implant bed preparation in surgery, for cooling in surgical areas and in septic surgery. This can significantly simplify, speed up and, above all, improve the effectiveness of numerous steps in surgical medicine.

Such cleansing assemblies consist essentially of a hand piece and a disposable flushing nozzle assembly or a disposable flushing nozzle unit. The disposable flushing nozzle unit consists of a base body and preferably a multi-part cleansing tube with a spray nozzle, on whose free end for example a spray guard can be provided. The base body is fastened to the hand piece, which preferably comprises a multi-part housing with a revolver or pistol grip-like cross section.

To create a pumping effect, a pump mechanism with a pump membrane is provided in the base body of the disposable flushing nozzle unit and is caused to pulse by means of a drive mechanism provided in the hand piece. In this design, the drive mechanism provided in the hand piece generates a pulsing motion in the area of the connection of the base body, which deflects the pump membrane extending into that area with a pre-defined frequency and therefore causes a pulsation of the pump membrane. The pulsation of the pump membrane in combination with the pump mechanism of the disposable flushing nozzle unit creates a pumping effect by means of which a cleansing or irrigating fluid from an external source is introduced through a hose system connected with the base body into the cleansing tube and through the latter into the respective surgical wound.

Prior art hand pieces feature a pneumatically operated motor, which is housed in the preferably multi-part housing. The compressed air required for operation of the motor unit is supplied to the hand piece by means of a bulky air hose. Such pneumatically operated hand pieces are equipped with efficient pneumatically operated motors, which at an operating pressure of 5-7 bar ensure optimal cleansing and/or irrigation of surgical wounds. A disadvantage, however, is that the bulky pneumatic hose required for this design hinders easy handling of the hand piece. Also, the cleansing power of prior art pneumatic hand pieces cannot be individually adapted to the respective surgical requirements.

Further, economically priced hand pieces designed as disposable items are known which are disposed of after a single use in the operating room. They feature an electric motor housed in the hand piece, however with lower power, and are equipped with an internal electric power supply housed in the hand piece, preferably in the form of several batteries or rechargeable batteries. The cleansing power of such economically priced hand piece designed as disposable items is limited, however, and often insufficient. It is also especially disadvantageous that the batteries or rechargeable batteries, e.g. of type AA or AAA, housed in the hand piece have to be replaced after a short time of about 3-5 minutes.

Based on the foregoing, an object of the invention is to present a hand piece for a disposable flushing nozzle unit for cleansing and/or irrigating surgical wounds which features improved handling and simultaneous high cleansing power.

SUMMARY OF THE INVENTION

The hand piece assembly according to the present invention includes a second connecting unit for connection of an external electric power supply, by means of which the electric motor integrated in the housing is supplied with electric power preferably with a high power output. The electric motor is supplied with electric power preferably by means of an external power pack, which is connected to the hand piece by means of a connecting cable via a plug-in connection. The elimination of the pneumatic air hose in combination with the energy supply according to the invention by means of a thin, flexible connecting cable of a power pack significantly improves ease of handling without, however, reducing the power output generated by the electric motor. In this respect the second connecting unit can be designed as a plug-in connector through which, for example, at least two different operating voltages can be present.

Also advantageously, a control unit is provided in the housing of the hand piece and is designed for operating the electric motor in at least two different power stages and/or two different operating modes, in particular interval and continuous operation. The control unit is provided for controlling the speed of the electric motor, namely in the range between 1200 and 5000 RPM. For example, a power stage can be provided for reduced pumping power, which can be selected for treatment of sensitive tissue or soft tissue in the field of plastic surgery. Alternatively or additionally, continuous operation can be selected, in which case the hand piece is operated without pressing the trigger. Especially in the case of infected (septic) operations this offers a special advantage over conventional hand pieces, namely the irrigation quantity can be increased and the surgeon has an additional hand free.

The drive mechanism is designed for converting a rotary motion of the electric motor into a pulsing translatory motion and preferably comprises at least one ram- or mushroom-shaped pushing element, one push rod element and one preferably cylindrical drive element, in which the drive element is functionally connected with the electric motor. The drive element in this design comprises a drive pin, which engages in a receiving hole provided in the push rod element.

It is especially advantageous that the hand piece can be re-sterilized. The hand piece comprises at least one switching means connected to the control unit, the switching means being functionally connected with one actuating means. Further, at least one display unit can be provided for displaying the operating mode and/or the power stage of the electric motor.

The invention is described below in more detail based on exemplary embodiments with reference to the drawings. Further embodiments, advantages and applications of the invention are also disclosed in the following description of the exemplary embodiments and the drawings. All characteristics described and/or pictorially represented, alone or in any combination, are subject matter of the invention, regardless of their being summarized or referenced in the claims. The content of the claims is also an integral part of the description. However, it is expressly noted that the invention is by no means limited to the exemplary embodiments provided. The invention is illustrated in the drawings.

DETAILED DESCRIPTION OF THE INVENTION

Figure 1:
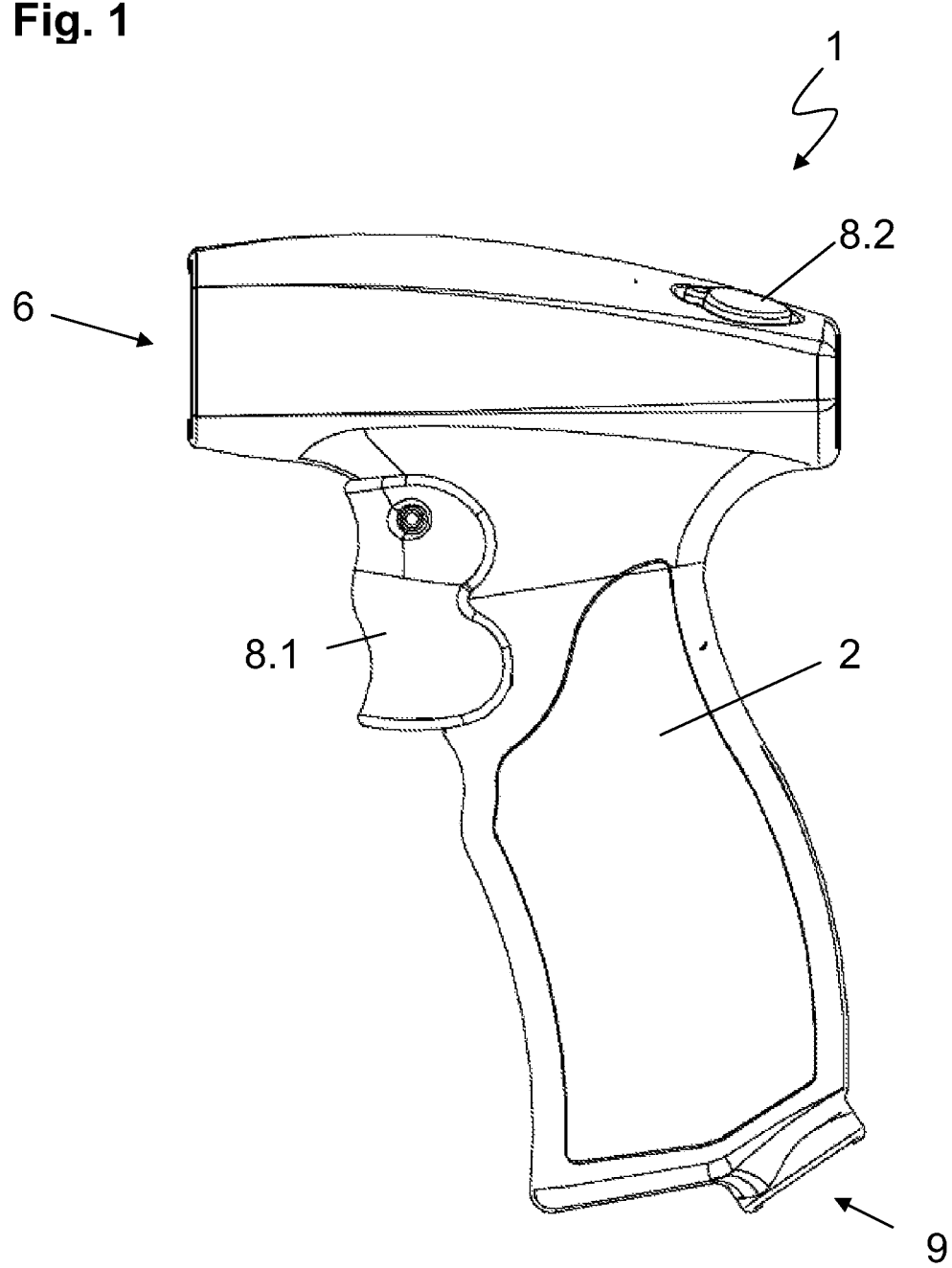
FIG. 1 is a schematic side view of a hand piece according to the invention.
Figure 2:
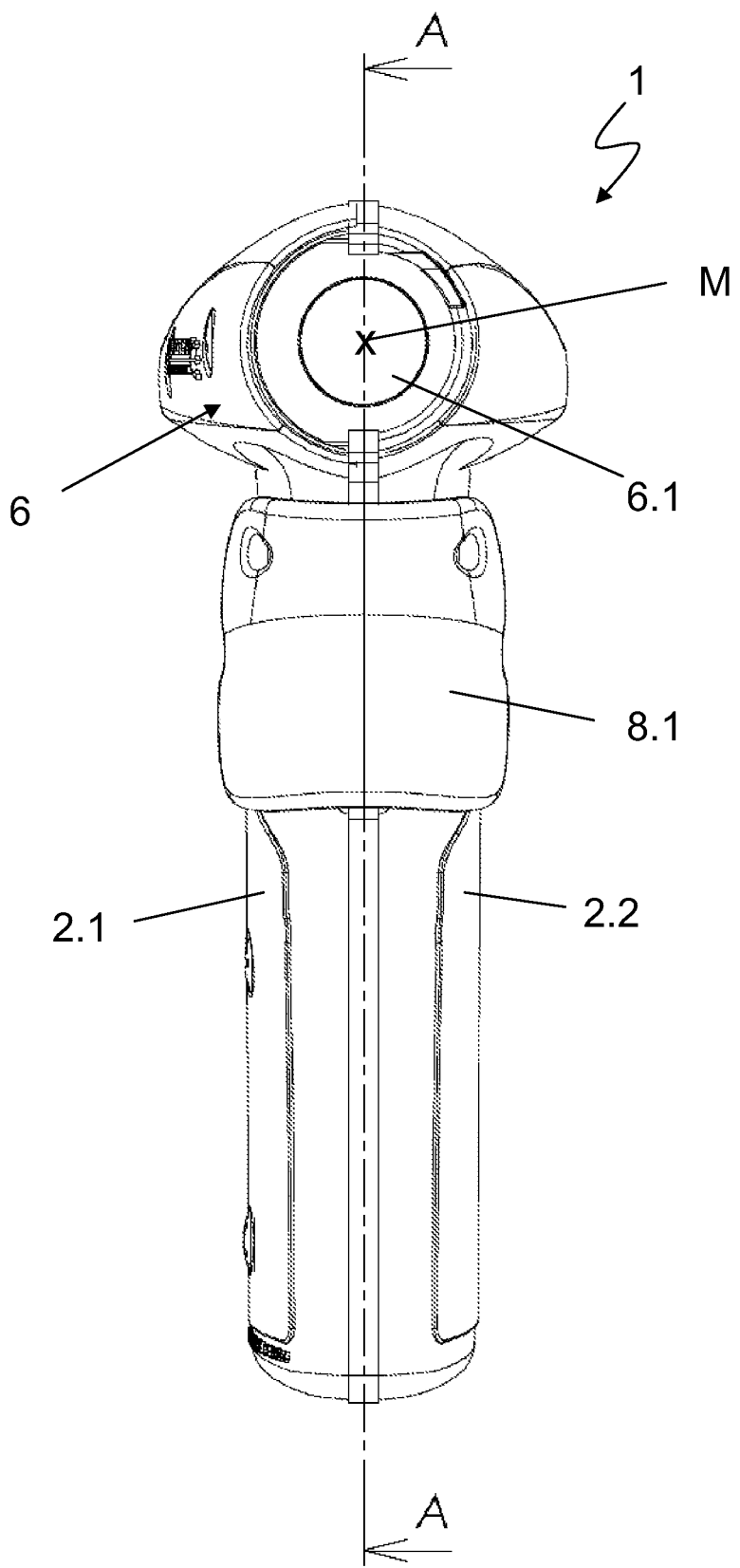
FIG. 2 is a front view of the hand piece according to the invention.
Figure 3:
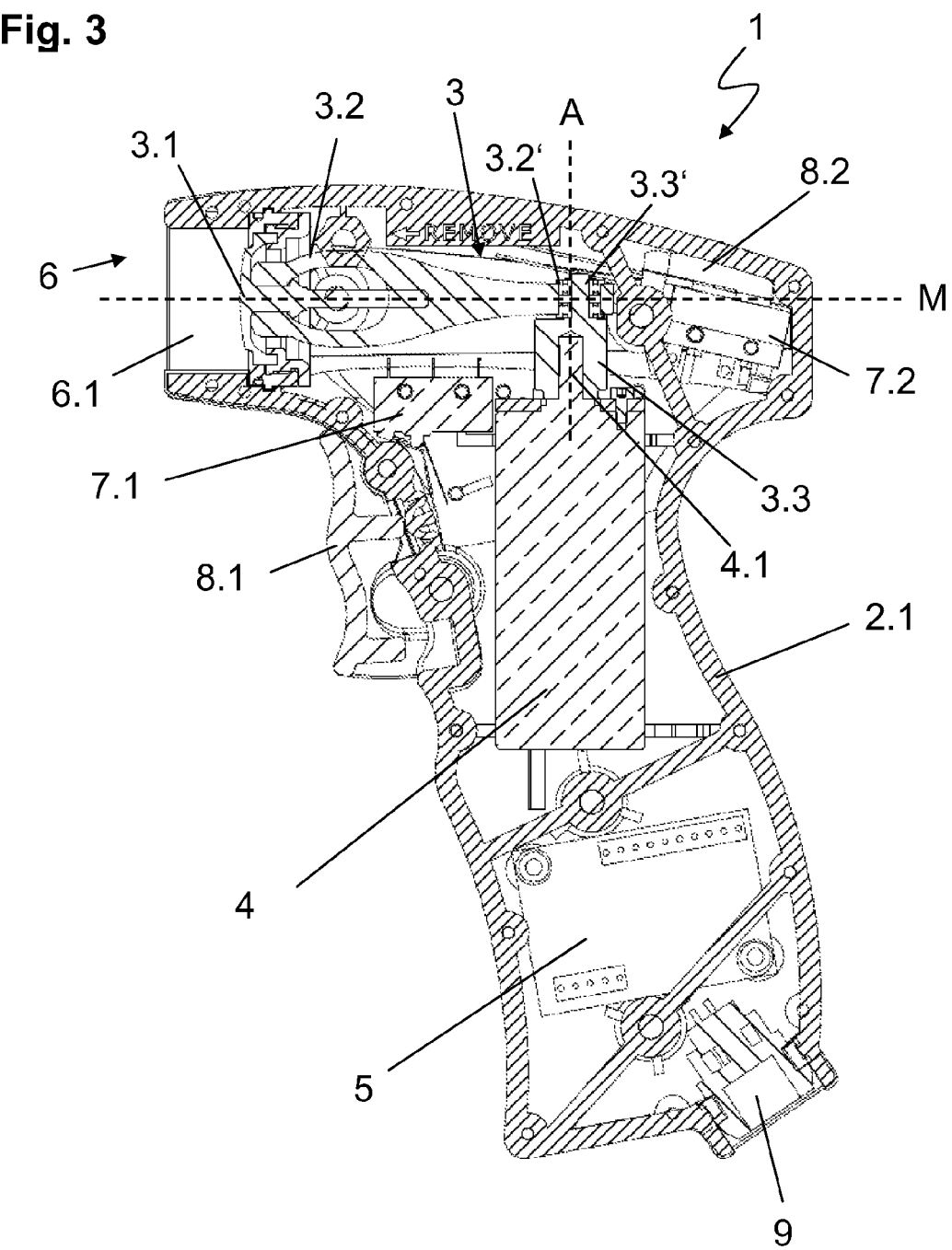
FIG. 3 is a longitudinal cross-sectional view taken along the line A-A through the hand piece according to the invention in FIG. 2.
Figure 4:
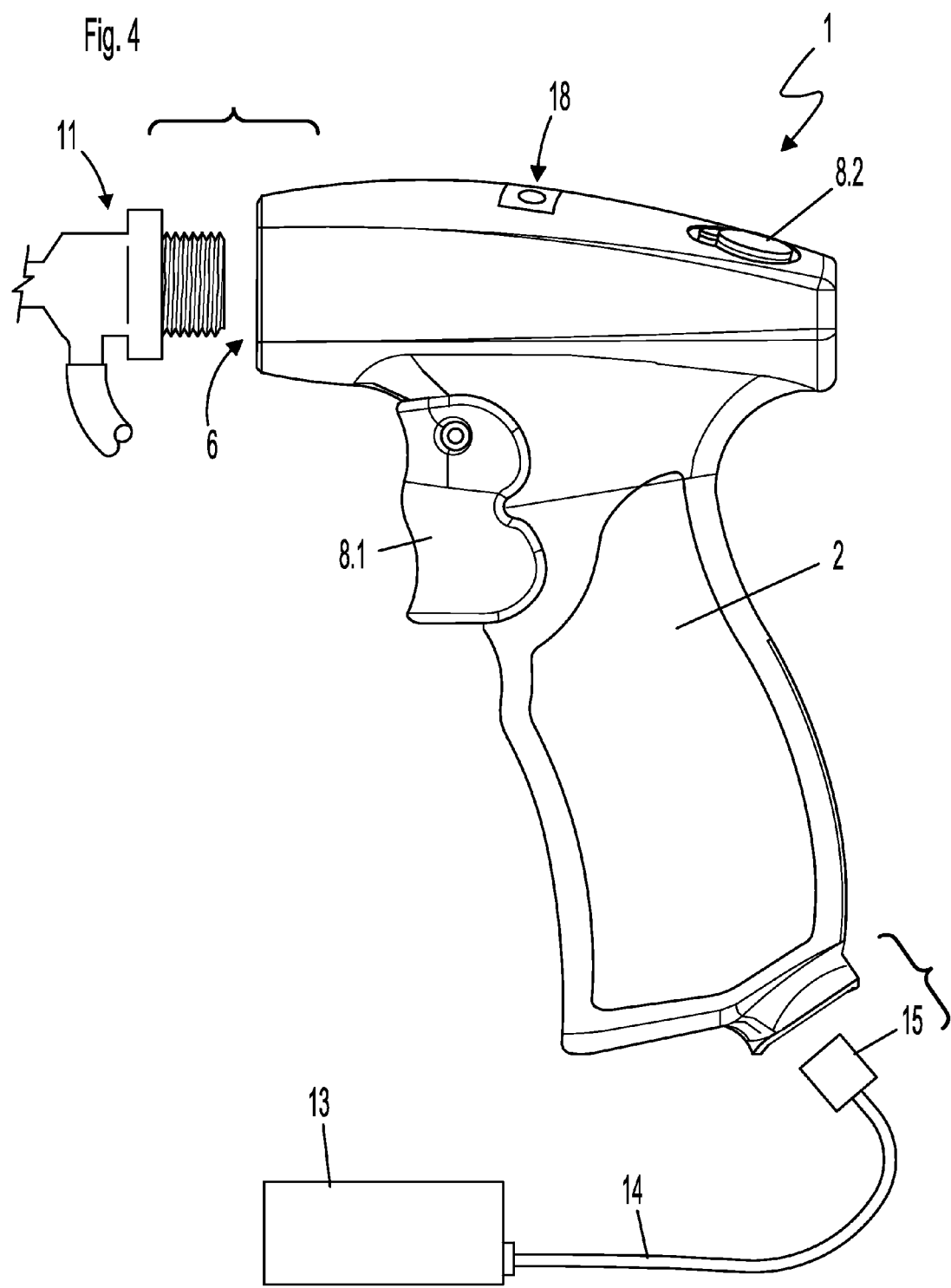
FIG. 4 is an exploded, schematic side view of a hand piece according to the invention having a display unit, a power supply and a nozzle connected thereto.

In the drawings, 1 generally designates a hand piece or hand piece assembly according to the invention for operating a disposable flushing nozzle or nozzle unit 11, depicted diagrammatically in FIG. 4 of the drawings, for cleansing and/or irrigating surgical wounds.

The hand piece 1 preferably comprises a multi-part housing 2, which is manufactured for example from metal or plastic or a combination of the above materials. The housing 2 in the present exemplary embodiment is a two-part housing and comprises a first housing half 2.1 and a second housing half 2.2, which respectively have a shell-like design. The first and second housing halves 2.1, 2.2 enclose a receiving space in which the various components of the hand piece 1 are housed. In a preferred embodiment the housing 2 has a revolver or pistol grip-shaped cross section and appearance. The housing 2 is likewise manufactured from a durable, especially non-breakable material which can be re-sterilized.

In the housing 2 of the hand piece 1, at least one drive mechanism 3 and one electric motor 4 interacting with the drive mechanism are provided, and for controlling the electric motor a controller or control unit 5 is provided, which preferably is housed in the lower grip area of the hand piece housing 2. The drive mechanism 3, on the other hand, is preferably housed in the upper grip area of the hand piece housing 2.

The hand piece 1 further is equipped with a first connecting unit, socket or receiver 6, which is designed for receiving a disposable flushing nozzle unit 11. More specifically, a connector or connecting section is provided on the base of the body of the nozzle unit for this purpose. The first connecting unit or nozzle receiver 6 comprises a recess 6.1 with a circular cross section, which is enclosed by the front-side free ends of the first and second housing halves 2.1, 2.2.

Preferably the nozzle receiver 6 includes inner threads, by means of which the connecting area of the disposable flushing nozzle unit, provided with outer threads, is fastened to the hand piece 1. It is to be understood that the connection between the nozzle unit 11 and the nozzle receiver may be formed by other means, including for example a bayonet connection.

The connector of the disposable flushing nozzle unit 11 is received in the recess 6.1 such that a pump membrane, which is provided in the connector of the disposable flushing nozzle unit 11 and which is externally accessible, operably interacts with the drive mechanism 3 of the hand piece assembly 1.

Further, switching means are provided in the hand piece 1 which interact with actuating means, by means of which the user of the hand piece 1 can vary the operating mode and/or the power output of the electric motor.

In the present exemplary embodiment, for example, at least first and second switching means such as switches 7.1, 7.2 are provided, which can be activated by means of first and second actuating means such as actuators 8.1, 8.2 provided in or on the housing 2. The first actuating means 8.1 is for example connected to one first switching means 7.1 and the second actuating means 8.2 with one second switching means 7.2, and the first and second switching means 7.1, 7.2 are connected to the control unit 5, which in turn is connected to the electric motor 4. The first actuating means 8.1 is implemented in the present exemplary embodiment in the form of a rocker switch, by means of which the hand piece 1 can be switched on or off. As the second switching means 7.2, two switches for example are provided on the top side of the housing 2 and are arranged symmetrically to the cutting plane A-A.

Further, the hand piece 1 comprises at least one second connecting unit, socket or receiver 9, which is provided in the lower grip area of the hand piece 1 or its housing 2. The second connecting unit 9 serves to electrically connect an external electric power supply 13 to the electrical components in the hand piece including the electric motor 4, control unit 5 and switches 7.1 and 7.2, and is preferably designed as a plug-in electrical socket. In particular, at least two different operating voltages can be present at the plug-in socket 9, which (voltages) can be selected respectively by means of the control unit 5 for operating the electric motor 4.

By means of the second connecting unit or socket 9, therefore, the hand piece 1 is supplied with the electric power, in particular operating voltage, required for operation of the electric motor 4 and the control unit 5. The external power source 13 is preferably formed by an electric power pack, which interacts with the socket 9 by means of a multi-wire electric connecting cable 14, on whose free end a plug connection 15 is provided. The electric motor unit is supplied in this manner for example with an operating voltage between 4.5 and 17.5 volts with an amperage of 0.5 to 0.8 A.

The power output of the electric motor unit is for example adjustable, namely at least two different power stages can be selected, for which the speed is in the range between 1200 and 5000 RPM. The drive mechanism 3 and the electric motor 4 interact in this design such that a pulsing translatory motion is generated in the area of the nozzle receiver 6, in particular within the circular recess 6.1, which acts upon the pump membrane of the disposable flushing nozzle unit and sets the latter in a corresponding pulsation, therefore creating a pumping effect of 5 to 15 ml/sec.

The drive mechanism 3 comprises a ram- or mushroom-shaped pushing element 3.1, which has a T-shaped cross section. The ram- or mushroom-shaped pushing element 3.1 is guided horizontally, namely along the center axis M of the circular recess 6.1. A push rod element 3.2 bears against the ram- or mushroom-shaped pushing element 3.1 and is mounted movably along the center axis M in the housing 2. The elongated part of the ram- or mushroom-shaped pushing element 3.1 is received in the front end of the push rod element 3.2, and on the opposite end of the push rod element 3.2 a receiving hole 3.2' is provided extending perpendicular to the center axis M, in which (receiving hole) a drive pin 3.3' of a drive element 3.3 engages and is movable mounted therein.

The drive element 3.3 is preferably cylindrical in shape and is provided for receiving a drive element 4.1 of the electric motor unit 4. The drive shaft 4.1 of the electric motor unit 4 is driven around or about the drive axis A, which preferably extends perpendicular to the center axis M. By means of the drive shaft 4.1 the cylindrical drive element 3.3 functionally connected with said drive shaft is set into a rotary motion around the drive axis A. The drive pin 3.3' of the drive element 3.3 in this design is eccentric to the drive axis A, so that the rotary motion of the drive element 3.3 is converted into a pulsing translatory motion of the push rod element 3.2 along the center axis M. Therefore, the drive mechanism 3 is provided for converting the rotary motion of the electric motor 4 into a pulsing translatory motion. This causes the electric motor 4 and the drive mechanism 3 to generate a pulsing translatory motion between 20 and 70 Hz, with which the pump membrane of the disposable flushing nozzle unit is impinged.

In a preferred embodiment the speed of the electric motor 4 can be adjusted by means of the control unit 5, namely in the range between 1200 and 5000 RPM. Preferably at least one first and second power stage are provided, which can be selected by means of the second switching means 7.2 or the actuating means 8.2 connected with said switching means 7.2. The electric motor 4 is put into operation by means of the first switching means 7.1 or the first actuating means 8.1, i.e. the hand piece is activated and the cleansing is started accordingly.

In a second embodiment, different operating modes of the electric motor 4 can be preset by means of the control unit 5, namely for example the electric motor 4 can be operated in interval or continuous operation. For this purpose, the user can select by means of corresponding actuation of the second actuating means 8.2 on the top side of the housing 2 whether the hand piece 1 should be able to be operated in continuous operation, i.e. without actuating the first switching means 8.1, or in interval operation, i.e. switched on or off based on actuation of the first actuating means 8.1. In addition, third actuating means and connected third switching means can be used to select between two power stages, in which case selecting the first power stage results in reduced pumping power from the hand piece 1 in the disposable flushing nozzle unit and selecting the second power stage results in maximum pump power from the hand piece 1 in the disposable flushing nozzle unit, i.e. the corresponding frequency of the pulsating translatory motion is increased or decreased accordingly.

For operation of the electric motor 4 in the first power stage it is supplied for example with an operating voltage of ca. 5 V and in the second power stage with an operating voltage of ca. 13.5 V. The electric motor 4 generates in the first power stage for example a power output of ca. 2.6 W and in the second power stage a power output of ca. 10.8 W. In consideration of the above, the speed of the electric motor 4 in the first power stage is ca. 1350 RPM and in the second power stage ca. 4150 RPM. Therefore, using a disposable flushing nozzle unit comprising a pump membrane, a pumping effect of ca. 7.5 ml/sec can be achieved in the first power stage and a pumping effect of ca. 15 ml/sec can be achieved in the second power stage.

In a further preferred embodiment, as shown in FIG. 4, the hand piece 1 comprises at least one display or display unit 18, which displays the selected operating mode and/or the selected power stage of the electric motor 4.

The display unit 18 can either be integrated in the second and third actuating means or can be designed separate from these. In a preferred embodiment the display unit 18 is implemented in the form of a light emitting diode or a lamp.

The hand piece 1 is preferably formed from a re-sterilizable material and watertight and therefore re-sterilizable.

The invention was described above based on an exemplary embodiment. It goes without saying that numerous modifications and variations of the invention are possible without abandoning the underlying inventive idea. For example, external power sources with different operating voltages can be used.

What is claimed is:

1. A hand piece for a disposable flushing nozzle for cleansing and/or irrigating surgical wounds, comprising:
    a housing with a first connecting unit for holding the disposable flushing nozzle;
    a drive mechanism and an electric motor interacting with said drive mechanism;
    a second connecting unit for connecting an external electric power supply;
    first and second switches for selecting a mode of operation and activating the electric motor; and
    a control unit provided in the housing and adapted for operating the electric motor in at least two different power stages, namely controlling the speed of the electric motor in the range between 1200 and 5000 RPM, and two different operating modes, a continuous operation mode selected by the second switch in which the electric motor is activated continuously regardless of actuation of the first switch, and an interval operation mode selected by the second switch in which the electric motor is activated or deactivated by the first switch, wherein the hand piece unit can be re-sterilized and the housing is manufactured from a re-sterilizable metal.

2. The hand piece according to claim 1, wherein said first and second switches are each operably connected with an actuator.

3. The hand piece according to claim 1, further comprising at least one display displaying the operating mode and/or the power stage of the electric motor.

4. An assembly comprising the hand piece as in claim 1 in combination with a disposable flushing nozzle unit and an external electric power source.

5. The assembly as in claim 4 wherein the external electric power source comprises an electric power pack with a plug-in connection.

6. The hand piece according to claim 1 wherein the drive mechanism converts a rotary motion of the electric motor into a pulsing translatory motion.

7. The hand piece unit according to claim 6, wherein the drive mechanism comprises at least one ram or mushroom shaped pushing element, one push rod element and one preferably cylindrical drive element, which is functionally connected with the electric motor.

8. The hand piece according to claim 7, characterized in that the drive element comprises a drive pin, which engages in a receiving hole provided in the push rod element.

9. A hand piece for a disposable flushing nozzle assembly for directing liquid under pressure to surgical wounds, comprising:
    a housing with a first connecting unit for connecting a disposable flushing nozzle assembly to said housing;
    an electric motor having a rotating drive shaft;
    a drive mechanism adapted to engage a disposable flushing nozzle assembly connected to said housing; said drive mechanism interacting with said electric motor drive shaft to convert a rotary motion of the electric motor drive shaft into a pulsing translatory motion;
    a second connecting unit for connecting an external electric power supply to said hand piece to supply electric power to said electric motor;
    first and second switches for selecting a mode of operation and activating the electric motor; and
    a control unit provided in the housing and adapted for operating the electric motor in at least two different power stages and two different operating modes, namely a continuous operation mode selected by the second switch in which the electric motor is activated continuously regardless of actuation of the first switch, and an interval operation mode selected by the second switch in which the electric motor is activated or deactivated by the first switch.

\* \* \* \* \*